(12) United States Patent
McCormick et al.

(10) Patent No.: US 12,290,523 B2
(45) Date of Patent: May 6, 2025

(54) FORMULATION OF LONG-ACTING LEVONORGESTREL BUTANOATE INJECTABLE DEPOT SUSPENSION

(71) Applicant: Eastern Virginia Medical School, Norfolk, VA (US)

(72) Inventors: Timothy J. McCormick, Wilmington, DE (US); Gustavo F. Doncel, Arlington, VA (US); Meredith Roberts Clark, Tuscaloosa, LA (US); Jill Schwartz, Garrett Park, MD (US)

(73) Assignee: Eastern Virginia Medical School, Norfolk, VA (US)

( * ) Notice: Subject to any disclaimer, the term of this patent is extended or adjusted under 35 U.S.C. 154(b) by 0 days.

(21) Appl. No.: 16/079,811

(22) PCT Filed: Feb. 23, 2017

(86) PCT No.: PCT/US2017/019092
§ 371 (c)(1),
(2) Date: Aug. 24, 2018

(87) PCT Pub. No.: WO2017/147274
PCT Pub. Date: Aug. 31, 2017

(65) Prior Publication Data
US 2019/0328749 A1    Oct. 31, 2019

Related U.S. Application Data

(60) Provisional application No. 62/299,257, filed on Aug. 24, 2018.

(51) Int. Cl.
*A61K 31/567* (2006.01)
*A61K 9/00* (2006.01)
(Continued)

(52) U.S. Cl.
CPC .......... *A61K 31/567* (2013.01); *A61K 9/0019* (2013.01); *A61K 9/10* (2013.01);
(Continued)

(58) Field of Classification Search
None
See application file for complete search history.

(56) References Cited

U.S. PATENT DOCUMENTS 3,919,411 A * 11/1975 Glass ..................... A61K 39/39
424/78.27
4,119,626 A    10/1978 Schulze et al.
(Continued)

FOREIGN PATENT DOCUMENTS

EP    0129947    1/1985

OTHER PUBLICATIONS

Hajikazemi et al. "Reason for discontinuation of depot medroxyprogesterone acetate", International Congress Series 1271, 315-318. (Year: 2004).*

(Continued)

*Primary Examiner* — Isis A Ghali
(74) *Attorney, Agent, or Firm* — Meunier Carlin & Curfman LLC (57) ABSTRACT

An improved long-acting injectable depot suspension formulation of LB displaying progestational effects which overcomes the aggregation and physical instability of LB injectable depot products, and also provides a longer duration of action of at least 4 months. Potential uses of this formulation include but are not limited to contraception and treatment or prevention of progestin/progesterone-sensitive reproductive tract dysfunctions and disorders.

10 Claims, 5 Drawing Sheets

(51) Int. Cl.
  A61K 9/10    (2006.01)
  A61K 47/02   (2006.01)
  A61K 47/10   (2017.01)
  A61K 47/26   (2006.01)
  A61K 47/38   (2006.01)

(52) U.S. Cl.
  CPC .............. *A61K 47/02* (2013.01); *A61K 47/10* (2013.01); *A61K 47/26* (2013.01); *A61K 47/38* (2013.01)

(56) References Cited

U.S. PATENT DOCUMENTS

| | | | |
|---|---|---|---|
| 4,794,119 | A | 12/1988 | Schulze et al. |
| 5,360,616 | A | 11/1994 | Garza Flores et al. |
| 9,168,264 | B2 | 10/2015 | Loumaye et al. |
| 2001/0051656 | A1 | 12/2001 | Place et al. |
| 2008/0220069 | A1 | 9/2008 | Allison |
| 2008/0317844 | A1 | 12/2008 | Dudley et al. |
| 2013/0018027 | A1 | 1/2013 | Podolski et al. |
| 2017/0290846 | A1* | 10/2017 | Lowe .................. A61K 9/0024 |

OTHER PUBLICATIONS

Reddy et al. "Principles of drug release in various dosage forms", Word Journal of Pharmaceutical Research; vol. 3, Issue 4, , 426-439. (Year: 2014).*

Gao et al. "Controlled release of a contraceptive steroid from biodegradable and injectable gel formulations: In vitro evaluation", Pharmaceutical Research, vol. 12, N0.6. (Year: 1995).*

Abuhanoğlu and Özer, "Radiation sterilization of new drug delivery systems," Interventional Medicine & Applied Science, 6(2), pp. 51-60 (2014).

Beetsma "The Differences Between Wetting Agents and Dispersants," Prospector, 4 pages (Apr. 10, 2015) <https://knowledge.ulprospector.com/2282/pc-differences-between-wetting-agents-and-dispersants/>.

ClinicalTrials.gov, "A Phase I Study to Evaluate the PK and PD of a Single Injection of Levonorgestrel Butanoate for Female Contraception (CCN011)," 4 pages, downloaded Apr. 4, 2016 <https://clinicaltrials.gov/show/NCT02173808>.

Conrad, "Product Development" 2 pages, downloaded Apr. 5, 2016 <http://www.conrad.org/microbicides-development.html>.

Coultas, "AstraZeneca's pediatric asthma medication patent held invalid as obvious," Intellectual Property Law Daily, pp. 1-3 (2015) <http://www.dailyreportingsuite.com/ip/news/astrazeneca_s_pediatric_asthma_medication_patent_held_invalid_as_obvious>.

Crabbé et al., "Long-acting contraceptive agents: Design of the who chemical synthesis programme," Steroids, 41(3) pp. 243-253 (1983).

Crosignani et al., "Levonorgestrel-releasing intrauterine device versus hysteroscopic endometrial resection in the treatment of dysfunctional uterine bleeding," Obstetrics & Gynecology, 90, pp. 257-263 (1997).

Edelman et al., "Levonorgestrel butanoate intramuscular injection does not reliably suppress ovulation for 90 days in obese and normal-BMI women: a pilot study," Author manuscript, published in final edited form as: Contraception, 95(1), pp. 55-58 (2017), 10 pages.

Garza-Flores et al., "Long-Acting Hormonal Contraceptives for Women," J. Steroid Biochem. Molec. Biol., 40, pp. 697-704 (1991).

Halpern et al., "Towards the development of a longer-acting injectable contraceptive: past research and current trends," Contraception, 92, pp. 3-9 (2015).

Jones and van de Wijgert, "DMPA use and HIV acquisition: time to switch to NET-EN?" Lancet HIV, 2(7), pp. E263-E264 (2015).

Noguchi et al., "Risk of HIV-1 Acquisition Among Women Who Use Different Types of Injectable Progestin Contraception in South Africa: A Prospective Cohort Study," Author manuscript, published in final edited form as: The Lancet HIV, 2(7), pp. E279-E287 (2015), 18 pages.

Puthli and Vavia, "Formulation and Performance Characterization of Radio-Sterilized "Progestin- Only" Microparticles Intended for Contraception," AAPS PharmSciTech, 10(2), pp. 443-452 (Jun. 2009).

Sherif, "Benefits and risks of oral contraceptives," Am. J. Obstet. Gynecol., 180(pt. 2), pp. S343-S348 (1999).

Wu et al., "Long-Acting Injectable Hormonal Dosage Forms for Contraception," Pharmaceutical Research, 32(7), pp. 2180-2191 (2015).

Bialy G et al., "Long-acting contraceptive agents: Structure activity relationships in a series of norethisterone and levonorgestrel esters", Steroids, Elsevier Science Publishers, New York, NY, US, vol. 41, No. 3, Mar. 1, 1983, pp. 419-439.

World Health Organization, Special Programme of Research, Development and Research Training in Human Reproduction: Annual Technical Report 1998. Geneva, WHO, 1999, 150 pages.

World Health Organization, Department of Reproductive Health and Research: Biennial Technical Report 2005-2006. Geneva, WHO, 2007, 223 pages.

Benagiano G et al., "The Special Programme of Research in Human Reproduction: Forty Years of Activities to Achieve Reproductive Health for All," Gynecol Obstet Invest 2012, 74:199.

Blithe D L, "Pipeline for Contraceptive Development," Fertil Steril 2016, 106(6):1298.

Examiner's Report issued in CA Application No. 3,015,781; dated Mar. 23, 2023; 3 pages.

* cited by examiner

FORMULATION OF LONG-ACTING LEVONORGESTREL BUTANOATE INJECTABLE DEPOT SUSPENSION

CROSS REFERENCE TO RELATED APPLICATION

This application is a National Stage Entry of PCT International Application No. PCT/US17/19092 filed Feb. 23, 2017, which claims the benefit of U.S. Provisional Application No. 62/299,257, dated Feb. 24, 2016, the contents of which are incorporated herein by reference in their entirety.

STATEMENT REGARDING FEDERALLY SPONSORED RESEARCH

This invention was made with government support under AID-OAA-A-15-0045 awarded by the U.S. Agency for International Development. The government has certain rights in the invention.

TECHNICAL FIELD OF THE INVENTION

The present invention relates to an improved formulation of a long-acting injectable depot suspension of Levonorgestrel Butanoate (LB) for contraceptive use and treatment or prevention of reproductive tract disorders.

BACKGROUND OF THE INVENTION

Contraceptive compositions based on esters of Levonorgestrel (LNG) have been disclosed in European Patent EP0129947B1. LNG is a safe and effective progestin contraceptive agent however its duration of action is relatively short when dosed orally and must be taken daily. LB is an esterified version of LNG with longer acting contraceptive properties especially when injected as an aqueous suspension depot formulation. Long-Acting Contraceptive Agents: Design of the WHO Chemical Synthesis Programme. Steroids. 1983 March; 41(3):243-53.

Progestin-only contraceptives are advantageous since they have a long-track record of safety and effectiveness and avoid estrogen-related side effects (Benefits and Risks of Oral Contraceptives. Am J Obstet Gynecol. 1999 June; 180(6 Pt 2):S343-8). Furthermore, long-acting progestin-only injectable contraceptives are desirable since they do not require daily dosing like oral contraceptives and are very effective when given at the required intervals. There are currently two injectable progestins, medroxyprogesterone acetate and norethindrone enanthate (also known as norethisterone enanthate), in use as long-acting contraceptive agents. Depot medroxyprogesterone acetate (DMPA) is an aqueous suspension depot formulation given at a dose of 150 mg (in 1 mL) every 3 months. Norethindrone enanthate (NET-EN) is formulated in an oil vehicle and given at a dose of 200 mg (in 1 mL) every 2 months.

More than 40 million women worldwide use injectable contraceptives. Use is particularly high in sub-Saharan Africa, where more than one-third of contraceptive users choose injectables. However, despite their popularity, discontinuation rates are high, often due to missed follow-up appointments. Currently available injectables are effective for only 1 to 3 months (depending on the formulation), requiring women to return to their provider 4 to 12 times per year. A longer acting injectable would help address this problem, as users would not have to return to the clinic as frequently for re-injections. Longer intervals between injections may lead to higher compliance and continuation rates (Development of a Longer-Acting Injectable Contraceptive. FHI 360, http://www.fhi360.org/projects/development-longer-acting-injectable-contraceptive).

Development of a long-acting LB injectable is particularly advantageous since LB is more potent than the two existing agents (DMPA and NET-EN) exerting its contraceptive activity for a longer period while allowing for a decreased steroid load. LB has been shown to suppress ovulation in women for 5-6 months when injected at a single dose of 50 mg formulated as a micronized aqueous suspension (Garza-Flores J, Hall P E, Perez-Palacios G. Long-Acting Hormonal Contraceptives for Women. *J Steroid Biochem Molec Biol* 1991; 40: 697-704). Unfortunately, earlier formulations of injectable LB were found to aggregate over time, resulting in loss of product stability and reproducibility of the clinical batches. A new stable formulation of LB has been developed and clinical testing at a dose of 20 mg (in 1 mL) showed a 3-month suppression of ovulation (Levonorgestrel Butanoate Intramuscular Injection Does Not Reliably Suppress Ovulation for 90 Days in Obese and Normal BMI Women: A Pilot Study, http://dx.doi.org/10.1016/j.contraception.2016.07.018). While the duration of action of new LB formulation is similar to that of DMPA and NET-EN, it falls short of the previously demonstrated 5-6 months and the preferred target product profile. Additional optimization of the formulation was conducted, and tested in non-human primates. With an improved and stable particle size formulation, duration of action up to 6 months was observed in non-human primates.

The decreased steroid load of LB may reduce the potential for undesirable side effects such as amenorrhea and hypoestrogenism which is frequently seen with DMPA. Unlike other progestins, DMPA is also increasingly being associated with higher risk for sexual HIV acquisition, possibly related to its significant hypoestrogenism (DMPA Use and HIV Acquisition: Time to Switch to NET-EN? *The Lancet HIV*, http://dx.doi.org/10.1016/S2352-3018(15)00076-4, Risk of HIV-1 Acquisition Among Women Who Use Different Types of Injectable Progestin Contraception in South Africa: A Prospective Cohort Study. The Lancet HIV, http://dx.doi.org/10.1016/S2352-3018(15)00058-2). LNG and LNG-derived injectables, such as LB, hold advantages of convenience and safety for women globally and in particular for those who are at high risk for sexual HIV transmission. In addition to contraception, long-acting progestins, such as LB, may be useful in the treatment or prevention of dysfunctional uterine bleeding, endometrial hyperplasia and cancer, endometriosis, fibroids, PMS, and other reproductive tract disorders.

SUMMARY OF THE INVENTION

An improved long-acting injectable depot suspension formulation of LB displaying progestational effects has been developed which overcomes the aggregation and physical instability of previous LB injectable depot products, and also provides a longer duration of action of at least 4 months. Potential uses of this formulation include but are not limited to contraception and treatment or prevention of progestin/progesterone-sensitive reproductive tract dysfunctions and disorders.

The present application discloses modified formulation compositions and manufacturing processes that address the limitations of earlier compositions.

In accordance with one embodiment, the present invention provides an extended duration injectable depot composition of Levonorgestrel Butanoate (LB) where the composition is a sterile aqueous depot suspension comprising non-aggregated LB particles with a median ($D_{50}$) particle size in the range of 5-50 µm, more particularly in the range of 10-30 µm and in other cases in the range of 13-35 µm, 13-40 µm, 13-50 µm, 15-35 µm, 15-40 µm, 15-50 µm, 20-35 µm, 20-40 µm, or 20-50 µm.

In some embodiments, the depot composition additionally comprises at least one ingredient selected from the group consisting of: surfactant(s), solubilizer(s), emulsifier(s), preservative(s), isotonicity agent(s), dispersing agent(s), wetting agent(s), filler(s), solvent(s), buffering agent(s), stabilizer(s), lubricant(s), thickening agent(s), flocculating agent(s), suspending agent(s), electrolytes, antioxidants, and chelating agent(s). In some embodiments, the depot composition comprises at least one of a wetting agent, a dispersing agent, a thickening agent, a buffering agent, and a preservative.

In some embodiments, the concentration of LB in the composition is 1-50 mg/mL and more particularly 10-20 mg/ml.

In accordance with one embodiment, a method of treating, ameliorating or preventing a progestin/progesterone-sensitive reproductive tract dysfunction or disorder is provided. The method comprises administering to a patient in need thereof a therapeutically effective amount of the depot composition disclosed herein. In some aspects, the dysfunction or disorder is selected from the group consisting of dysfunctional uterine bleeding, endometrial hyperplasia and cancer, endometriosis, fibroids, and PMS.

In accordance with one embodiment, a method of providing long term contraception is provided. The method comprises administering to a patient in need thereof a therapeutically effective amount of the depot composition disclosed herein. In some embodiments, the depot provides an extended duration of progestational action of at least 4 months. In some cases, the progestational action effects contraceptive activity for an extended duration of at least 4 months.

In some embodiments, the depot composition comprises a wetting agent and/or dispersing agent selected from the group consisting of polyethoxylated sorbitan fatty acid esters, sorbitan fatty acid esters, polyoxyalkylene derivatives of propylene glycol, phosphatides, lecithin, polyoxyethylated fats, polyoxyethylated oleotriglycerides, linolizated oleotriglycerides, polyethylene oxide condensation products of fatty alcohols, and alkyphenols.

In some embodiments, the depot composition comprises polysorbate 80.

In some embodiments, the depot composition comprises a wetting agent. In some cases, the wetting agent is present in the composition at a concentration in the range of 0.05-2% w/v and more particularly 0.2% w/v.

In some embodiments, the dispersing agent comprises sorbitan monopalmitate.

In some embodiments, the depot composition comprises a dispersing agent. In some cases, the dispersing agent is present in the composition at a concentration in the range of 0.05-2% w/v and preferably 0.2% w/v.

In some embodiments, the depot composition comprises at least one thickening agent. In some cases, the thickening agent is selected from the group consisting of sodium carboxymethyl cellulose, methyl cellulose, hydroxypropyl cellulose, calcium carboxymethyl cellulose, crosslinked carboxymethyl cellulose, hydroxyethylcellulose, hydroxypropylmethyl cellulose, polyvinyl alcohol, acacia, gelatin, and polyvinyl pyrrolidone.

In some embodiments, the depot composition comprises a thickening agent, which is present in the composition at a concentration in the range of 0.1-5% w/v and preferably 0.5-1.0% w/v. In some embodiments, the thickening agent comprises sodium carboxymethyl cellulose.

In some embodiments, the depot composition comprises at least one preservative. In some cases, the preservative is selected from the group consisting of benzyl alcohol, parabens, methyl paraben, propyl paraben, butyl paraben, benzalkonium chloride, thiomerosal, phenol, meta-cresol, chlorobutanol, phenylmercuric salts, phenylmercuric acetate, phenylmercuric borate, and phenylmercuric nitrate.

In some embodiments, the preservative comprises benzyl alcohol.

In some embodiments, the depot composition comprises a preservative, which is present in the composition at a concentration in the range of 0.1-5% v/v and preferably 1.0% v/v.

In some embodiments, the depot composition comprises at least one buffer. In some cases, the buffer is selected from the group consisting of acetate, citrate, tartrate, phosphate, and triethanolamine (TRIS).

In some embodiments, the buffer comprises phosphate.

In some embodiments, a method of producing a sterile injectable depot composition of Levonorgestrel Butanoate is provided. In some embodiments, the method comprises subjecting Levonorgestrel Butanoate to a size reduction and sterilization process to yield sterile micronized Levonorgestrel Butanoate with a median ($D_{50}$) particle size in the range of 5-50 µm, more particularly in the range of 10-30 µm and in other cases in the range of 13-35 µm, 13-40 µm, 13-50 µm, 15-35 µm, 15-40 µm, 15-50 µm, 20-35 µm, 20-40 µm, or 20-50 µm and combining the sterile micronized Levonorgestrel Butanoate with a sterile aqueous vehicle to form the sterile injectable depot composition.

In some embodiments, the sterile micronized Levonorgestrel Butanoate is produced by sterile filtration and recrystallization followed by aseptic micronization.

In some embodiments, the sterile micronized Levonorgestrel Butanoate is produced by non-sterile dry or wet milling followed by gamma or e-beam irradiation sterilization.

In some embodiments, the sterile micronized Levonorgestrel Butanoate is produced by non-sterile spray drying followed by gamma or e-beam irradiation sterilization.

In some embodiments, the method includes preparing a first sterile aqueous solution comprising at least one pharmaceutically acceptable ingredient selected from the group consisting of a thickening agent, a buffering agent, and a preservative; preparing a second sterile aqueous solution comprising at least one pharmaceutically acceptable ingredient selected from the group consisting of a wetting agent and a dispersing agent; dispersing the sterile micronized Levonorgestrel Butanoate in the second sterile aqueous solution; and combining the second sterile aqueous solution containing the sterile micronized Levonorgestrel Butanoate with the first sterile aqueous solution to form the final sterile injectable depot composition.

In some embodiments, the first sterile aqueous solution comprises a thickening agent, buffering agent, and preservative.

In some embodiments, preparing the first sterile aqueous solution comprises adding the preservative to water for injection at a temperature of ≤10° C.; and dissolving the thickening agent in the water for injection containing the preservative. Following dissolution of the thickening agent, the buffering agent is added and dissolved.

In some embodiments, the second sterile aqueous solution comprises a wetting agent and dispersing agent.

In some embodiments, preparing the second sterile aqueous solution comprises adding the wetting agent and dispersing agent to water for injection; and homogenizing the mixture of wetting agent, dispersing agent, and water for injection to uniformly disperse the dispersing agent.

In some embodiments, combining the second sterile aqueous solution containing the sterile micronized Levonorgestrel Butanoate with the first sterile aqueous solution comprises adding the first sterile aqueous solution to the second sterile aqueous solution containing the sterile micronized Levonorgestrel Butanoate; and homogenizing the combined solutions to form a uniformly dispersed Levonorgestrel Butanoate suspension.

BRIEF DESCRIPTION OF THE DRAWINGS

The following figures are provided for the purpose of illustration only and are not intended to be limiting.

DETAILED DESCRIPTION OF THE INVENTION

In accordance with one aspect, the present invention provides an improved formulation and process for preparation of a long-acting injectable depot suspension formulation of LB.

With previous LB suspension formulations, aggregation or clumping of the micronized particles, and adhesion of the particles to the glass ampoules during storage, were observed, causing the physical instability of the product. Therefore, studies to evaluate various LB suspension formulations were performed in order to improve the physical stability of the suspension formulation. The results of these studies indicated that a formulation containing micronized LB within certain particle ranges and at least one dispersing and/or wetting agent (e.g., 0.2% w/v each of Tween® 80 (polysorbate 80) and Span® 40 (sorbitan monopalmitate)) corrected these problems and exhibited the most acceptable physical stability with respect to appearance, particle size distribution, resuspendability, and syringeability of the micronized steroid.

As used herein, the term "ameliorating" refers to the lessening, decrease, or diminishing of a symptom, state, or condition. In one aspect, a symptom of a disease is ameliorated when the symptom decreases in severity of occurrence or effect in a patient. In another aspect, a symptom of a disease is ameliorated when the symptom is completely eradicated or eliminated from the patient.

The term "preventing" as used herein refers to delaying and/or precluding the onset of a disorder, disease, or condition, and/or its attendant symptom(s); keeping a subject from acquiring a disease; or reducing a subject's risk of acquiring a disorder, disease, or condition.

The term "treating" in relation to the present invention refers to preventing, curing, reversing, attenuating, alleviating, minimizing, suppressing, or halting the deleterious effects of a disease state, disease progression, or other abnormal condition. For example, treatment may involve alleviating a symptom (i.e., not necessarily all symptoms) of a disease or attenuating the progression of a disease.

In one embodiment of the present invention, the improved formulation and process comprises the following steps: Non-sterile, unmicronized LB drug substance first undergoes the process of sterile filtration and recrystallization. The process involves dissolving the levonorgestrel butanoate in dichloromethane or another suitable solvent and sterile filtering the solution. The levonorgestrel butanoate is then recrystallized from the sterile filtered solution, for example, in a rotary evaporator and washed with ethanol or other suitable solvent to reduce the amount of residual dichloromethane. The sterile filtered and recrystallized drug substance is then sterile micronized. The sterile micronization process involves reducing the particle size of the sterile filtered and recrystallized LB drug substance, such as by milling, under aseptic conditions to yield a median ($D_{50}$) particle size for the LB that is in the range of 5-50 µm, more particularly in the range of 10-30 µm and in other cases in the range of 13-35 µm, 13-40 µm, 13-50 µm, 15-35 µm, 15-40 µm, 15-50 µm, 20-35 µm, 20-40 µm, or 20-50 µm.

In another embodiment of the present invention, non-sterile unmicronized LB drug substance is first milled (dry or wet) under non-aseptic conditions to yield a median ($D_{50}$) particle size for the LB that is in the range of 5-50 µm followed by sterilization using either gamma or e-beam irradiation to produce the sterile micronized LB drug substance. In accordance with certain aspects, the particle size is in the range of 10-30 µm and in other cases in the range of 13-35 µm, 13-40 µm, 13-50 µm, 15-35 µm, 15-40 µm, 15-50 µm, 20-35 µm, 20-40 µm, or 20-50 µm.

In another embodiment of the present invention, non-sterile unmicronized LB drug substance is dissolved in dichloromethane or other suitable solvent followed by evaporation of the solvent by spraying the LB solution into a drying chamber to produce a median ($D_{50}$) particle size for the LB that is in the range of 5-50 µm, more particularly in the range of 10-30 µm and in other cases in the range of 13-35 µm, 13-40 µm, 13-50 µm, 15-35 µm, 15-40 µm, 15-50 µm, 20-35 µm, 20-40 µm, or 20-50 µm. The spray dried micronized LB drug substance is then sterilized using either gamma or e-beam irradiation to produce the sterile micronized LB drug substance.

The sterile micronized LB is then formulated into a sterile aqueous vehicle to form the final sterile injectable suspension product. In accordance with a certain aspect, the sterile aqueous vehicle comprises: a wetting agent, a dispersing agent, a thickener, a buffering agent, and a preservative. In accordance with a certain aspect, the sterile aqueous vehicle comprises: polysorbate 80 (Tween® 80), sorbitan monopalmitate (Span® 40), sodium carboxymethyl cellulose, sodium phosphate dibasic anhydrous, sodium phosphate monobasic dihydrate, and benzyl alcohol.

In another embodiment of the present invention, manufacturing of the sterile LB injectable suspension is conducted in two parts. The first part (Part I) comprises a sterile aqueous solution of a thickener (e.g., sodium carboxymethyl cellulose), buffering agent (e.g., sodium phosphate dibasic anhydrous, sodium phosphate monobasic dihydrate), and a preservative (e.g., benzyl alcohol). The second part (Part II) contains a sterile aqueous solution of a wetting agent (e.g., polysorbate 80) and dispersing agent (e.g., sorbitan monopalmitate). The Part I solution contributes to approximately 50-95%, more particularly about 60-80%, 70-80% or 75% of the total batch size of the active suspension while the Part II solution contributes approximately 5-50%, 15-35%, 15-25% or 20%. The sterile micronized levonorgestrel butanoate drug substance is aseptically added into the sterile Part II solution and mixed until dispersed. The sterile Part I solution is then aseptically added with mixing to the sterile Part II solution containing the LB to form the final drug product suspension. The final drug product suspension is then aseptically homogenized to ensure uniformity of the suspension. The final drug product suspension is then aseptically filled into an appropriate container such as a sealed vial or prefilled syringe for final use.

The process of making the suspension formulation was also modified to improve the blend uniformity and physical stability of the drug product. Specifically, the order of addition of the LB and the formulation components has been modified along with the dispersion/mixing and homogenization of the LB and formulation components. The micronized LB is first mixed into a solution containing the wetting and dispersion agents. A separate solution is also prepared to dissolve the thickening agent, the buffering agents, and the preservative. These two separate solutions are then mixed together and homogenized to produce a uniform LB suspension product.

Furthermore, the viscosity of the formulation has been modified to improve the physical stability of the suspension in terms of the settling rate of the LB particles. Slower settling rates are particularly important during the drug product manufacturing process to ensure product consistency and uniformity when holding and transferring the final bulk suspension product for downstream operations such as in-process sampling and testing, filling, etc.

Figure 1:
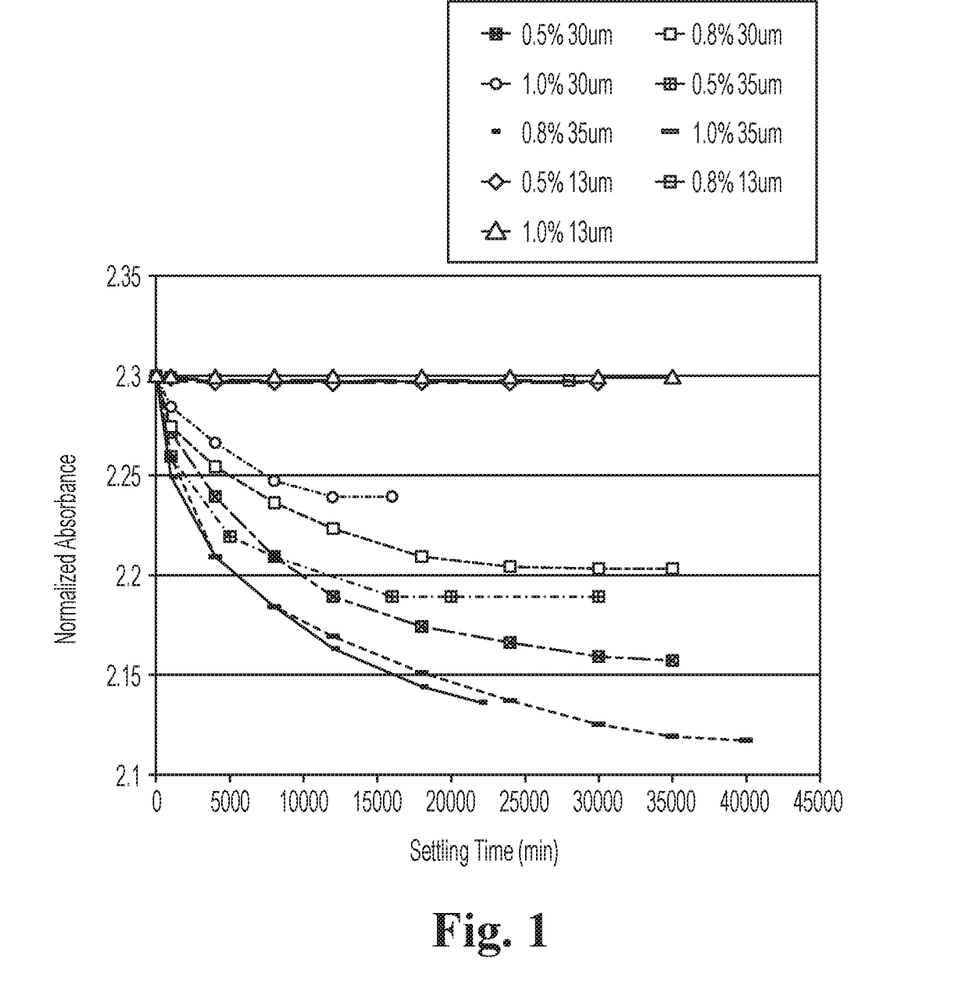
FIG. 1 shows the results of a settling time study demonstrating that a sodium carboxymethyl cellulose concentration of 0.5-1.0% in the formulation is particularly useful for minimizing the effects of settling of the LB particles in the improved LB injectable depot suspension formulation.
Figure 2:
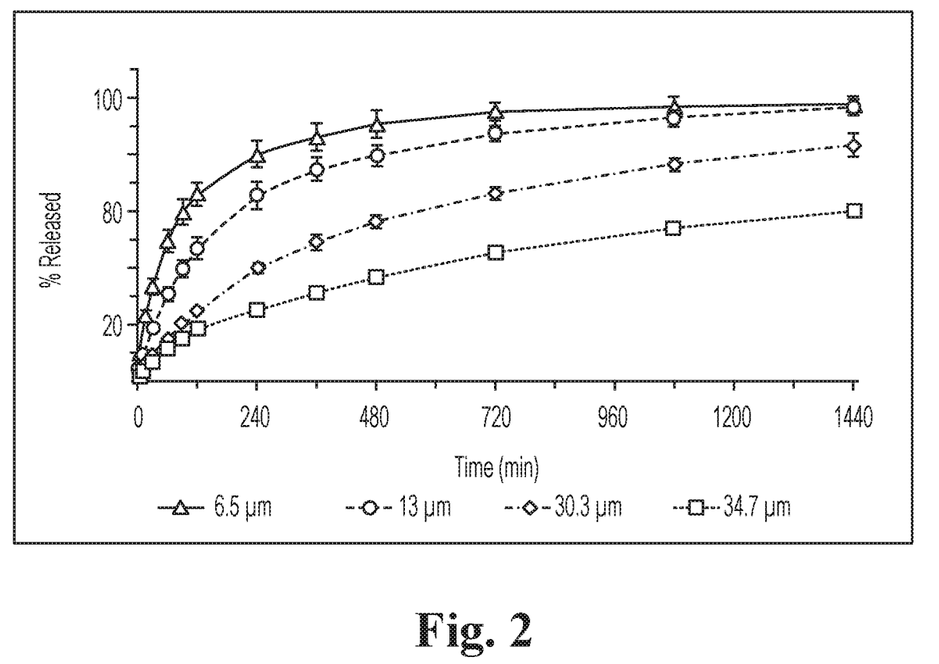
FIG. 2 shows the in vitro release data for the improved LB injectable depot suspension formulation micronized to different particle size ranges, demonstrating longer release of larger particle size LB formulations.

FIG. 1 shows the results of a settling time study demonstrating that a sodium carboxymethyl cellulose (NaCMC) concentration of 0.5-1.0% in the formulation is optimal for minimizing the effects of settling of the LB particles from the suspension. There was essentially no settling for a 13 μm LB particle size formulation observed at any concentration of NaCMC. For a 30 μm LB particle size formulation the settling rate decreased with increasing NaCMC concentration. With a 35 μm LB particle size formulation, 0.8% and 1.0% concentrations of NaCMC resulted in similar settling rates while settling in the 0.5% NaCMC solution was apparently slower, but initial rates were similar. Overall, different settling rates of LB from the suspension were observed with different particle sizes of the LB drug substance and different concentrations of NaCMC. However, the general trend is that a NaCMC concentration of 0.5-1.0% in the formulation is particularly useful for providing decreased settling rates of LB in the suspension for LB particle sizes ranging from $D_{50}$ of 13-35 μm.

In addition to improvements made to the final drug product formulation and manufacturing processes, improvements were also made in the duration of action of the product by increasing the median ($D_{50}$) particle size of the LB drug substance in the formulation.

FIG. 2 shows the in vitro release data for the improved LB injectable depot formulation micronized to different particle size ranges ($D_{50}$), demonstrating longer in vitro release rates for formulations prepared with larger particle sized LB drug substance. The plot provides in vitro release data (mean of n=3±S.D.) for the improved LB injectable depot suspension formulation containing LB drug substance micronized to different particle sizes. In vitro release was conducted using a flow through cell in a closed-loop mode with phosphate buffered saline pH 7.4 containing 0.75% sodium lauryl sulfate at 37° C. as the test medium and a flow rate of 20 mL/minute. A monkey study has demonstrated that the time to return to ovulation increases with increasing particle size of LB in the formulation and in many cases exceeding six months. The $D_{50}$=6.5 μm particle size formulation was also tested in humans at a 20 mg dose level and showed a 3-month suppression of ovulation. Therefore, longer suppression of ovulation (of at least 4 months) will also be achieved in humans with the larger particle size LB ($D_{50}$=13-35 μm) formulations.

The process of preparing the sterile micronized LB drug substance by sterile filtration and recrystallization followed by sterile micronization can also be improved to increase the efficiency and scalability of this part of the manufacturing process. An alternative process for preparing the sterile micronized LB drug substance consists of first subjecting non-sterile, non-micronized LB drug substance to size reduction processes such as dry-milling or wet-milling or spray drying to achieve the desired particle size followed by sterilization of the micronized LB via gamma or e-beam irradiation.

EXAMPLES

Example 1

An LB injectable depot suspension formulation comprising the following:

TABLE 1

| Ingredient | Function | % w/v |
|---|---|---|
| Levonorgestrel Butanoate, sterile micronized (median particle size (D50): 5-50 μm) | Active ingredient | 1-2 |
| Super Refined Polysorbate 80, NF | Wetting agent | 0.2 |
| Sorbitan Monopalmitate, NF spray dried | Dispersing agent | 0.2 |
| Sodium carboxymethyl cellulose, medium viscosity fine grade: 7MFPH, USP | Thickening agent | 0.5-1.0 |
| Sodium phosphate dibasic anhydrous, USP | Buffering agent | 0.3 |
| Sodium phosphate monobasic, dihydrate, USP | Buffering agent | 1.49 |
| Benzyl alcohol, NF | Preservative | 1% v/v |
| Sterile Water for Injection, USP | Bulk Medium | q.s. 100% |

Example 2

The sterile Part I solution can be prepared by adding a portion (~30%) of cold (≤10° C.) water for injection (WFI) to a mixing vessel and then adding benzoyl alcohol to the cold WFI in the vessel and stirring for 5 minutes. While mixing, slowly adding sodium carboxymethyl cellulose (NaCMC), medium viscosity fine grade in small aliquots to the vessel and mixing until visually completely dissolved. Once the NaCMC is visually dissolved the remaining WFI (at room temperature) is slowly added to the vessel and the solution is mixed for approximately 1.5 hours. Sodium phosphate dibasic anhydrous is then added to the vessel, while mixing, and the solution is then mixed until dissolved. Sodium phosphate monobasic dihydrate is then added to the vessel, while mixing, and the solution is then mixed until dissolved. The final Part I solution is then sterile filtered to produce a sterile solution.

Example 3

The sterile Part II solution can be prepared by adding a portion (~87.5%) of WFI to a mixing vessel and then adding polysorbate 80 to the WFI in the vessel and stirring for approximately 20 minutes. Sorbitan monopalmitate is then added to the vessel and the mixture is homogenized at approximately 3000 rpm for a minimum of 45 minutes until the sorbitan monopalmitate is dispersed. Once the sorbitan monopalmitate is dispersed the remaining WFI is added to the vessel and the solution is mixed for a minimum of 10 minutes. The final Part II solution is then autoclaved to produce a sterile solution.

Example 4

The final sterile LB drug product suspension can be prepared by placing the sterile Part II solution into a sterile mixing vessel in an aseptic environment and then slowly adding, in small portions (approximately 0.5 g per minute), the sterile micronized LB to the sterile Part II solution in the vessel while mixing. Allow the LB to completely disperse after each addition before beginning the next addition. After the final addition of LB continue mixing for an additional 15-30 minutes. While mixing, slowly add the sterile Part I solution to the vessel over an approximately 5 minute period. Continue mixing for a minimum of 15 minutes. Q.S. the suspension with WFI and continue mixing for approximately 30 minutes. Homogenize the final sterile LB suspension at 3500 rpm for a minimum of 2 hours. With continuous mixing, aseptically fill the sterile homogenized LB suspension into an appropriate sterile container (e.g., sealed vial, prefilled syringe, etc.) for final use.

Example 5

A LB injectable depot suspension formulation comprising the same composition as in Example 1 except with the LB micronized via milling or spray drying under non-sterile conditions and then sterilized by e-beam or gamma irradiation.

Table 2 shows the physical stability data for the improved LB injectable depot suspension formulation containing wetting and/or dispersing agents, Tween® 80 (polysorbate 80) and Span® 40 (sorbitan monopalmitate) (0.2% each), demonstrating lack of particle size growth and aggregation of the product over a two year period when stored at 25° C. and 65% relative humidity. The suspension sediment is easily redispersed with gently swirling and inversion and the redispersed suspension maintains its ability to be withdrawn by a 23-gauge syringe.

TABLE 2

Levonorgestrel Butanoate Injectable Suspension, 20 mg/mL

| Storage Condition: 25° C./60% RH | | Packaging: 2 mL of suspension in a 3 mL clear glass vial with stopper and crimp cap seal Time Point (Months) | | | | |
|---|---|---|---|---|---|---|
| Test | Specification | 0 | 6 | 12 | 18 | 24 |
| Appearance | Clear, colorless supernatant with sediment that gives a white uniform suspension | Conforms | Conforms | Conforms | Conforms | Conforms |
| Particle Size | Report Results for D10, D50, D90, and VMD (Volume Mean Diameter) in μm | 1.4<br>6.3<br>17.6<br>8.2 | 1.3<br>6.2<br>17.9<br>8.3 | 1.4<br>6.5<br>19.9<br>9.0 | 1.4<br>6.3<br>19.1<br>8.7 | 1.4<br>6.4<br>18.1<br>8.5 |
| Resuspendibility | While swirling, invert the vial gently to redisperse the suspension. Record the number of inversions needed to completely redisperse the suspension. | 15 | 27 | 40 | 28 | 51 |

TABLE 2-continued Levonorgestrel Butanoate Injectable Suspension, 20 mg/mL

| Storage Condition: 25° C./60% RH | Packaging: 2 mL of suspension in a 3 mL clear glass vial with stopper and crimp cap seal Time Point (Months) | | | | |
|---|---|---|---|---|---|
| Test | Specification | 0 | 6 | 12 | 18 | 24 |
| Syringeability | The suspension can be withdrawn by a 23 gauge syringe | Conforms | Conforms | Conforms | Conforms | Conforms |

Table 3 shows the results of the modified dispersion/mixing and homogenization processes for the improved manufacturing process for the improved LB injectable depot suspension formulation demonstrating the effectiveness of the dispersion/mixing and homogenization process steps. More specifically, Table 3 shows the uniformity of the LB particle size distribution and concentration following dispersion and mixing of the micronized LB with the formulation components followed by homogenization of the final LB suspension product. The data shows that a uniform mixture is obtained within 15-30 minutes of mixing following dispersion of the LB and the formulation components into solution. In addition, the final suspension product continues to maintain its uniformity following 74-144 minutes of homogenization.

TABLE 3

Post LB Dispersion in Part II & Mixing with Part I

| Elapsed Time (Minutes) | Particle Size (μm) | | | |
|---|---|---|---|---|
| | $D_{10}$ | $D_{50}$ | $D_{90}$ | VMD[1] |
| 15 | 1.4 | 6.3 | 17.1 | 8.1 |
| 30 | 1.4 | 6.3 | 17.2 | 8.1 |

Assay Results - Concentration of LB (mg/mL)

| | Average | SD[2] | % RSD[3] |
|---|---|---|---|
| 15 | 20.03 | 0.13 | 0.7 |
| 30 | 20.00 | 0.08 | 0.4 |

Homogenization of Final Drug Product

| | Particle Size (μm) | | | |
|---|---|---|---|---|
| | $D_{10}$ | $D_{50}$ | $D_{90}$ | VMD |
| 74 | 1.4 | 6.4 | 18.4 | 8.5 |
| 144 | 1.4 | 6.6 | 20.1 | 9.0 |

Assay Results - Concentration of LB (mg/mL)

| | Average | SD | % RSD |
|---|---|---|---|
| 74 | 19.94 | 0.17 | 0.8 |
| 144 | 19.67 | 0.23 | 1.1 |

[1]Volume Mean Diameter
[2]Standard Deviation
[3]Relative Standard Deviation

Figure 3:
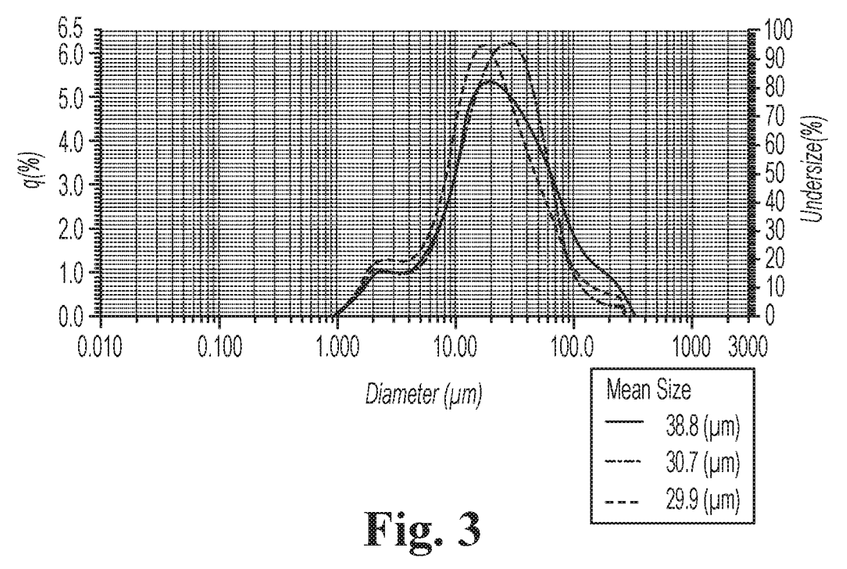
FIG. 3 shows the particle size distribution obtained from dry milled levonorgestrel butanoate drug substance.
Figure 4:
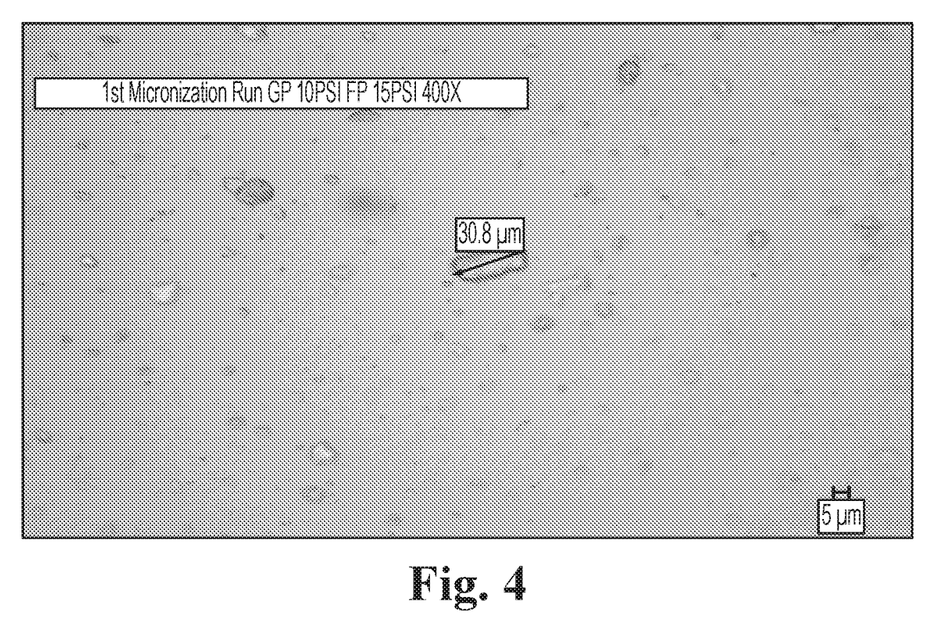
FIG. 4 is a photomicrograph showing the particle size distribution obtained from dry milled levonorgestrel butanoate drug substance.

FIG. 3 and FIG. 4 show typical particle size distributions and photomicrographs of LB drug substance prepared by dry milling. The dry milled LB powder was dispersed in 1% polysorbate 20 and three replicate measurements of the particle size distribution were made. Results for particle size (μm) are provided in Table 4.

| Run | Mean | $D_{10}$ | Median | $D_{90}$ |
|---|---|---|---|---|
| 1 | 38.6 | 5.3 | 23.1 | 89.5 |
| 2 | 30.7 | 5.1 | 22.7 | 62.2 |
| 3 | 29.9 | 4.3 | 18.6 | 65.0 |

Figure 5:
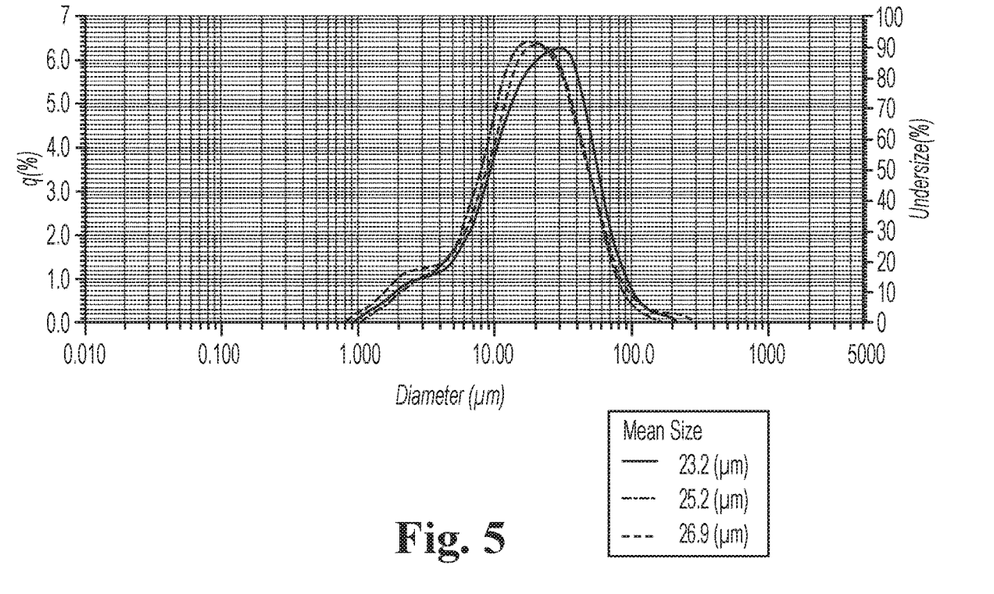
FIG. 5 shows the particle size distribution obtained from rotor-stator wet milled (10% w/w suspension of LB in aqueous 0.05% Tween 80) levonorgestrel butanoate drug substance.
Figure 6:
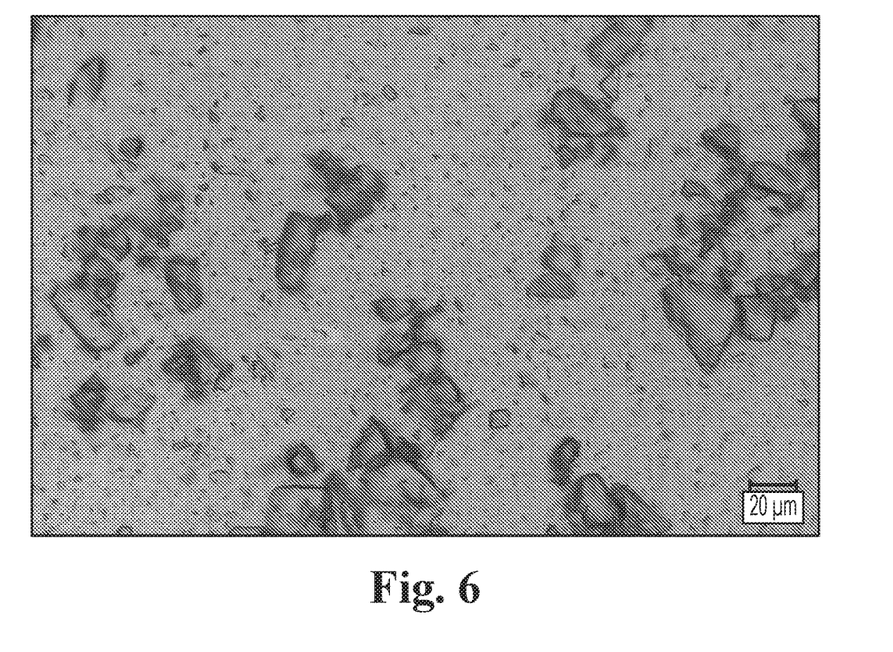
FIG. 6 is a photomicrograph showing the particle size distribution obtained from rotor-stator wet milled (10% w/w suspension of LB in aqueous 0.05% Tween 80) levonorgestrel butanoate drug substance.

FIG. 5 and FIG. 6 show typical particle size distributions and photomicrographs of LB drug substance prepared by wet milling. After wet milling for 15 minutes, the LB suspension was sampled and three replicate measurements of the particle size distribution were made. Results for particle size (μm) are provided in Table 5.

| Run | Mean | $D_{10}$ | Median | $D_{90}$ |
|---|---|---|---|---|
| 1 | 23.2 | 5.4 | 18.0 | 47.3 |
| 2 | 25.2 | 4.3 | 18.4 | 50.9 |
| 3 | 26.9 | 5.4 | 21.0 | 54.9 |

Figure 7:
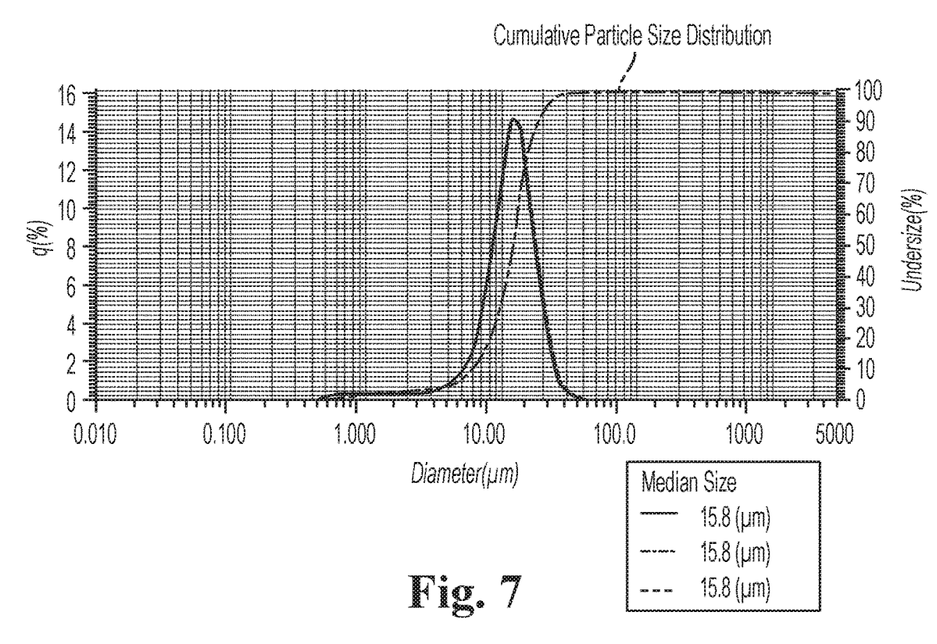
FIG. 7 shows the particle size distribution obtained from spray dried (5% w/w solution of LB in dichloromethane) levonorgestrel butanoate drug substance.
Figure 8:
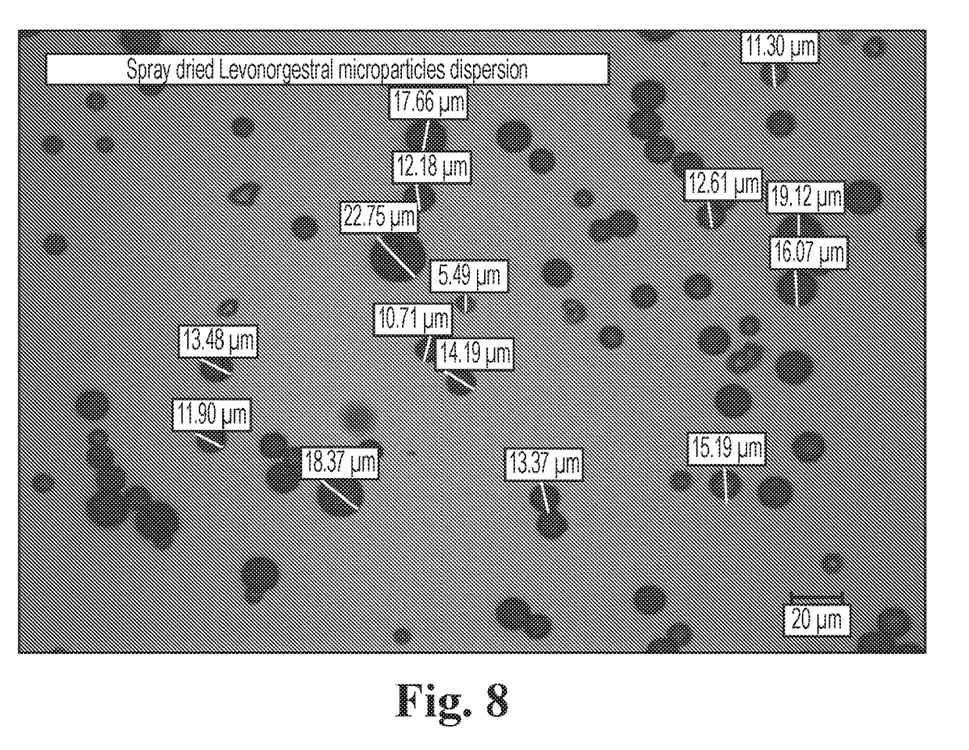
FIG. 8 is a photomicrograph showing the particle size distribution obtained from spray dried (5% w/w solution of LB in dichloromethane) levonorgestrel butanoate drug substance.

FIG. 7 and FIG. 8 show typical particle size distributions and photomicrographs of LB drug substance prepared by spray drying processes. The spray dried LB powder was dispersed in 0.5% polysorbate 80 and three replicate measurements of the particle size distribution were made. Results for particle size (μm) are provided in Table 5.

| Run | $D_{10}$ | Median | $D_{90}$ |
|---|---|---|---|
| 1 | 8.3 | 15.8 | 24.7 |
| 2 | 8.2 | 15.8 | 24.8 |
| 3 | 8.2 | 15.8 | 24.8 |

The invention being thus described, it will be apparent that the same may be varied in many ways. Such variations are not to be regarded as a departure from the spirit and scope of the invention, and all such modifications as would be recognized by one skilled in the art are intended to be included within the scope of the present application.

What is claimed is:

1. An injectable composition of Levonorgestrel Butanoate (LB),
    wherein the composition is a sterile aqueous suspension comprising LB particles with a median ($D_{50}$) particle size in the range of 13-50 μm,
    wherein the composition comprises polysorbate 80 and sorbitan monopalmitate,
    wherein polysorbate 80 is present in the composition at a concentration in the range of 0.05-2% w/v, wherein sorbitan monopalmitate is present in the composition at a concentration in the range of 0.05-2% w/v, wherein the composition shows a lack of particle size growth and aggregation over a two-year period when stored at 25° C. and 65% relative humidity, and wherein the composition provides an extended duration of progestational action of at least 4 months.

2. The composition according to claim 1, wherein the concentration of LB in the composition is 1-50 mg/mL.

3. The composition according to claim 1, wherein the composition further comprises at least one thickening agent from the group consisting of sodium carboxymethyl cellulose, methyl cellulose, hydroxypropyl cellulose, calcium carboxymethyl cellulose, crosslinked carboxymethyl cellulose, hydroxyethylcellulose, hydroxypropylmethyl cellulose, polyvinyl alcohol, acacia, gelatin, and polyvinyl pyrrolidone.

4. The composition according to claim 3, wherein the at least one thickening agent comprises sodium carboxymethyl cellulose.

5. The composition according to claim 4, wherein the thickening agent is present in the composition at a concentration in the range of 0.1-5% w/v.

6. The composition according to claim 1, wherein the composition further comprises at least one preservative selected from the group consisting of benzyl alcohol, parabens, methyl paraben, propyl paraben, butyl paraben, benzalkonium chloride, thiomerosal, phenol, meta-cresol, chlorobutanol, phenylmercuric salts, phenylmercuric acetate, phenylmercuric borate, and phenylmercuric nitrate.

7. The composition according to claim 6, wherein the at least one preservative comprises benzyl alcohol.

8. The composition according to claim 6, wherein the preservative is present in the composition at a concentration in the range of 0.1-5% v/v.

9. The composition to claim 1, wherein the composition further comprises at least one buffer selected from the group consisting of acetate, citrate, tartrate, phosphate, and triethanolamine (TRIS).

10. The composition according to claim 9, wherein the at least one buffer comprises phosphate.

* * * * *

UNITED STATES PATENT AND TRADEMARK OFFICE
CERTIFICATE OF CORRECTION

PATENT NO. : 12,290,523 B2
APPLICATION NO. : 16/079811
DATED : May 6, 2025
INVENTOR(S) : Timothy J. McCormick et al.

It is certified that error appears in the above-identified patent and that said Letters Patent is hereby corrected as shown below:

On the Title Page

First Column, in the Related U.S. Application Data section after Item (60), replace "Provisional application No. 62/299,257, filed on Aug. 24, 2018." with --Provisional application No. 62/299,257, filed on Feb. 24, 2016.--

Signed and Sealed this
Sixteenth Day of September, 2025

Coke Morgan Stewart
*Acting Director of the United States Patent and Trademark Office*